United States Patent [19]

Nakajima et al.

[11] Patent Number: 5,348,552
[45] Date of Patent: Sep. 20, 1994

[54] LASER SURGICAL UNIT

[75] Inventors: Sadahiro Nakajima; Naoshi Endoh, both of Tokyo; Kenzo Kataoka; Masaki Odaka, both of Kyoto, all of Japan

[73] Assignees: Hoya Corporation, Tokyo; Kabushiki Kaisha Morita Seisakusho, Kyoto, both of Japan

[21] Appl. No.: 936,047

[22] Filed: Aug. 26, 1992

[30] Foreign Application Priority Data

Aug. 30, 1991 [JP]  Japan ................................. 3-219484

[51] Int. Cl.$^5$ .......................................... A61B 17/36
[52] U.S. Cl. ..................................... 606/13; 606/16; 606/28; 607/89
[58] Field of Search ............................. 128/395–398; 606/13–16, 27, 28; 607/89, 96

[56] References Cited

U.S. PATENT DOCUMENTS

| 4,736,743 | 4/1988 | Daikuzono | 606/28 |
| 4,832,979 | 5/1989 | Hoshino | 606/28 |
| 4,917,084 | 4/1990 | Sinofsky | 128/398 |

FOREIGN PATENT DOCUMENTS

| 2060397 | 5/1981 | United Kingdom | 606/28 |
| 2244650 | 12/1991 | United Kingdom | 606/28 |

*Primary Examiner*—Stephen C. Pellegrino
*Assistant Examiner*—M. Peffley
*Attorney, Agent, or Firm*—Ladas & Parry

[57] ABSTRACT

In a laser surgical unit having a contact laser probe (1), a hydroxyl group (13) is included in the contact laser probe so that a laser beam is partially absorbed by the hydroxyl group (13) to heat the contact laser probe (1) for transmission to living tissue. Consequently, a coagulation layer is formed in the living tissue along with vaporization and incision. At least a part of the contact laser probe (1) is made of a material which contains the hydroxyl group (13) generally in an amount of between 0.5 and 10 ppm. Alternatively, the hydroxyl group (13) may be included only in a portion adjacent to a surface of a tip portion of the probe (1). As a further alternative, a coating film containing the hydroxyl group (13) may be attached to the tip of the contact laser probe (1). The laser beam preferably has a wavelength between 1.5 and 15 μm. For example, use is made of an Er:YAG laser beam, a Ho:YAG laser beam, or a $CO_2$ laser beam. The laser surgical unit of the above-mentioned structure is excellent in manipulatability, capable of safely and uniformly cutting living tissue, and capable of successively performing hemostasis.

7 Claims, 5 Drawing Sheets

LASER SURGICAL UNIT

BACKGROUND OF THE INVENTION

This invention relates to a laser surgical unit for converging a laser beam onto a diseased part of a living tissue in an organism, such as a human body, to perform a surgical operation.

A laser surgical unit of the type described has been used in a surgical operation to remove a diseased part by a laser beam emitted therefrom. More specifically, when the laser beam is irradiated onto the diseased part of a living tissue, beam absorption, temperature elevation, vaporization, incision, coagulation, and hemostasis successively take place in the living tissue. On the beam absorption in the living tissue, the laser beam is transformed into thermal energy. The thermal energy heats water in the living tissue to cause vaporization to occur. In this event, a surface of the living tissue is heated to a high temperature at which the coagulation layer is formed. Due to the vaporization, the surface of the living tissue is expanded and ruptured to thereby perform incision of the living tissue. The coagulation layer serves to perform hemostasis.

Such laser surgical units are classified into contact and non-contact laser surgical units which comprise contact and non-contact laser probes, respectively.

As contact and noncontact laser surgical units, use has been made either for a $CO_2$ (carbon dioxide gas) laser surgical unit which comprises a non-contact laser probe or for a Nd (neodymium) laser surgical unit which comprises a contact laser probe.

Specifically, the $CO_2$ laser surgical unit generates a laser beam at an oscillation wavelength of 10 $\mu$m. Such a laser beam is highly absorbed in a hydroxyl group (OH) which is rich in a living tissue. This is because the non-contact laser probe is included in the $CO_2$ laser surgical unit to emit the laser beam onto the living tissue and to cause the laser beam to be directly absorbed in the living tissue. Consequently, the living tissue itself is heated to cause vaporization to occur in the living tissue. Thus, incision is performed.

On the other hand, the Nd laser surgical unit generates a laser beam at an oscillation wavelength of 1 $\mu$m. Such a laser beam is low in absorption in the living tissue. If a high absorption material for the laser beam, for example manganese dioxide, is coated on the entire surface of the contact laser probe so as to absorb the laser beam, the tip of the contact laser probe itself is heated. For example, such an Nd laser surgical unit is disclosed in Japanese Patent Prepublication No. 318934/1988. Incision and hemostasis are performed with the probe heated to a high temperature.

The $CO_2$ laser surgical unit mentioned above provides a beautiful cut surface because the $CO_2$ laser surgical unit generates the laser beam highly absorbed in the living tissue. However, most of the energy of the laser beam is consumed in vaporization because of its high absorptivity in the living tissue. Therefore, the living tissue is insufficiently heated. As a result, a coagulation layer of a sufficient thickness can not be formed. Thus, the $CO_2$ laser surgical unit has a degraded hemostatic ability.

Since the $CO_2$ laser surgical unit is of a non-contact type, a surgeon or an operator can not feel by sense of touch in a surgical operation. It is therefore difficult to perform uniform incision with the laser beam constantly focused along a cutting line.

On the other hand, the Nd laser surgical unit performs incision by the use of a heat generated in the coating film on a tip portion of the contact laser probe. A coagulation layer of an appropriate thickness is formed. Thus, hemostasis and incision are performed. However, the coating film on the tip portion of the contact laser probe is often exfoliated due to heat. If the coating film is exfoliated, the contact laser probe suffers variation in the heat generated at the surface of the contact laser probe. This results in fluctuation of cutting ability of the contact laser probe to unfavorably provide a variable sense of touch felt by the operator. When incision is carried out by the use of such a contact laser probe, the operator may be affected by the variable sense of touch to produce an operation error, for example, in the cutting rate. In the presence of the operation error, the living tissue is overheated to form a nonuniform coagulation layer having a too thick portion or a too deep portion.

SUMMARY OF THE INVENTION

It is therefore an object of this invention to provide a laser surgical unit which is excellent in manipulatability, which is capable of safely and uniformly cutting living tissue, and which can perform hemostasis with excellent reliability.

A laser surgical unit to which this invention is applicable is for use in a surgical operation to perform vaporization and incision by emitting a laser beam, and comprises a contact laser probe for emitting the laser beam. According to this invention, the contact laser probe includes a specific portion which comprises a hydroxyl group at a rate such that the contact laser probe is heated enough to perform the surgical operation and that the laser beam is emitted from the contact laser probe so as to perform the vaporization and the incision.

Preferably, the contact laser probe includes a specific portion which comprises a hydroxyl group at a rate between 0.5 and 10 ppm.

Preferably, the contact laser probe has a support portion and a tip portion supported by the support portion to emit the laser beam through the tip portion, wherein the specific portion is restricted to the tip portion.

Preferably, the specific portion is restricted to a surficial area of the contact laser probe.

Preferably, the tip portion is coated with a coating film containing the hydroxyl group.

Preferably, the laser beam has a wavelength between 1.5 through 15 $\mu$m.

Preferably, the laser beam is selected from a group consisting of an Er:YAG laser beam, a Ho:YAG laser beam, and a $CO_2$ laser beam.

A laser therapeutic method according to this invention comprises the steps of preparing a contact laser probe including a hydroxyl group at a rate between 0.5 and 10 ppm, bringing a contact laser probe into contact with an object, generating a laser beam from the contact laser probe, and irradiating the object by the laser beam to perform vaporization and incision with the contact laser probe heated by absorbing the remainder of the laser beam in the contact laser probe, to perform hemostasis.

As described, a part of the laser beam is emitted from the contact laser probe as an outgoing laser beam while the remainder of the laser beam is absorbed in the hydroxyl group contained in the contact laser probe to heat the contact laser probe. In a surgical operation, the outgoing laser beam serves to cause vaporization and incision of the living tissue to occur while the contact laser probe thus heated is brought into contact with a cut portion to form a coagulation layer for hemostasis.

The contact laser probe partially contains the hydroxyl group in a tip of the contact laser probe or in a surface of the tip. With this structure, the tip of the contact laser probe is heated while the laser beam is effectively emitted. The similar effect is obtained in the case where the coating film containing the hydroxyl group is applied on the tip of the contact laser probe.

The laser beam has a wavelength between 1.5 and 15 $\mu$m and is absorbed in the hydroxyl group to heat the contact laser probe. Thus, a coagulation layer is formed to perform hemostasis. It is noted that an Er:YAG laser beam, a Ho:YAG laser beam, or a $CO_2$ laser beam have wavelengths within the above-mentioned range.

DESCRIPTION OF THE PREFERRED EMBODIMENTS

Figure 1:
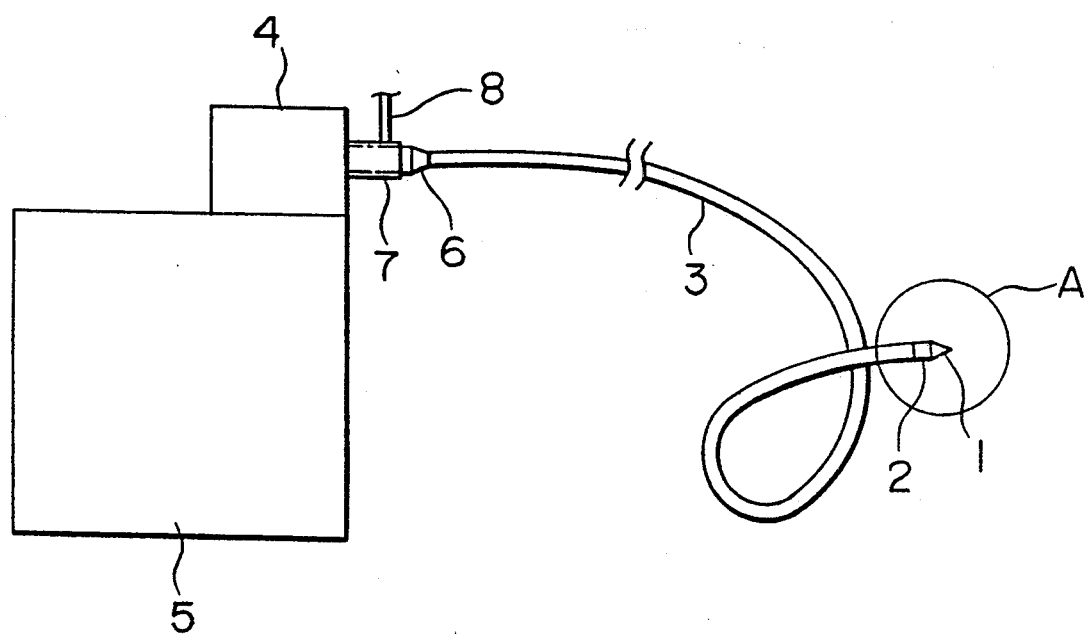
FIG. 1 is a diagrammatic view describing the structure of a laser surgical unit according to an embodiment of this invention.

Now, description will be made as regards several embodiments of this invention with reference to the drawing.

Referring to FIG. 1, a laser surgical unit is shown which comprises a laser probe 1, a probe coupler 2, a laser beam transmitter 3, a laser oscillator 4, and a laser controller 5.

The laser probe 1 is connected through the probe coupler 2 to one end of the laser beam transmitter 3. The other end of the laser beam transmitter 3 is connected through a connector 6 to a socket 7 in the laser oscillator 4.

The laser oscillator 4 may be an Er:YAG laser, a Ho:YAG laser, or a $CO_2$ laser. These lasers generate a laser beam in a wavelength range between 1.5–15 $\mu$m which is highly absorbed in a hydroxyl group.

Figure 2:
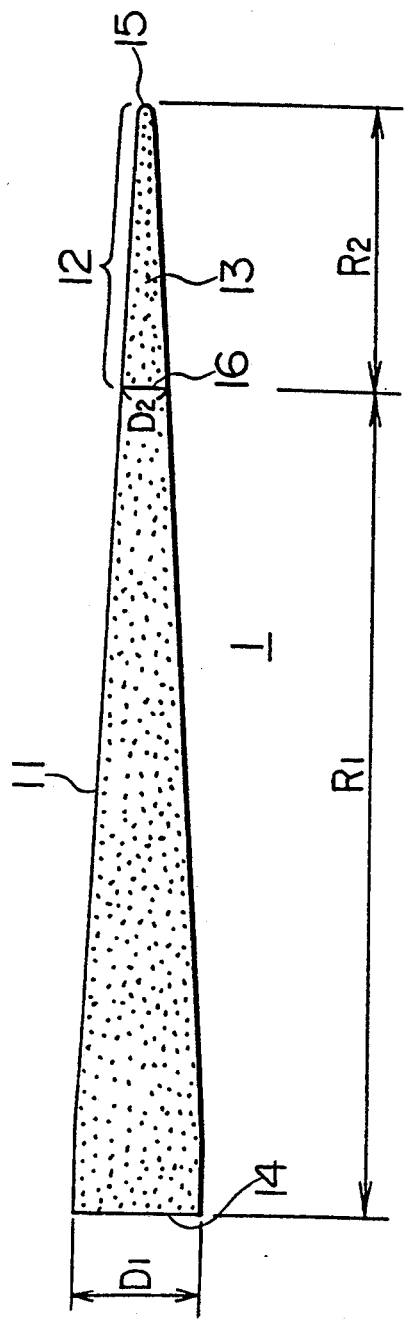
FIG. 2 is a side view of a contact laser probe for use in the laser surgical unit illustrated in FIG. 1.

Referring to FIG. 2, the contact laser probe 1 of a contact type consists of a rod member of conical shape gradually tapered from a base end (a leftmost portion in the figure) to a tip end or extremity. The base end and the tip end define an incident end 14 and a probe tip 15, respectively. Specifically, the contact laser probe 1 comprises an optical guide portion 11 and an operating portion 12. The optical guide portion 11 is adjacent to the base end and is for guiding an incident laser beam from the incident end 14 towards the probe tip 15. The operating portion 12 adjacent to the tip end is for simultaneously carrying out incision and hemostasis when brought into contact with a living tissue.

The contact laser probe 1 is made of a basic material which can transmit a laser beam of the type used. In this embodiment, an Er:YAG laser is used which oscillates at an oscillation wavelength of 2.94 $\mu$m. Accordingly, the basic material is selected so as to transmit an Er:YAG laser beam. In this embodiment, quartz glass is used as the basic material. Alternatively, use may be made of other glass materials, such as chalcogenide glass and fluoride glass, or crystallized materials, such as calcium fluoride, sapphire, and zinc selenide. These materials can also be used for a Ho:YAG laser which oscillates at an oscillation wavelength of 2.1 $\mu$m. For a $CO_2$ laser which oscillates at an oscillation wavelength of 10.6 $\mu$m, use is made of glass materials, such as chalcogenide glass, or crystallized materials, such as zinc selenide.

In the contact laser probe 1, the incident end 14 has an outer diameter D1 which is equal to 2 mm. An incident end 16 of the operating portion 12 has an outer diameter D2 which is equal to 0.8 mm. The optical guide portion 11 has a length R1 which is equal to 15 mm. The operating portion 12 has a length R2 which is equal to 5 mm.

Table 1 shows a relationship between a rate or concentration of the hydroxyl group and an emitting rate of the laser beam emitted from the operating portion 12 as well as a temperature of the operating portion 12. The contact laser probe has the dimensions mentioned above. The laser beam is generated by an Er:YAG laser and has a wavelength of 2.94 $\mu$m. In this event, the laser beam has an output of 100 millijoules and is produced at 10 pps. It is understood from Table 1 that the concentration of the hydroxyl group must be 0.5 ppm or more in order to heat the operating portion 12 to 60° C. at which a coagulation layer is formed for hemostasis. On the other hand, when the concentration of the hydroxyl group is not smaller than 30 ppm, the laser beam can not be emitted out from the operating portion 12. In this event, it is impossible to perform incision of the living tissue by the use of the laser beam. At this time, most of the laser beam is absorbed in the incident end 14 of the contact laser probe 1 including the hydroxyl group at a concentration greater than 30 ppm. This results in a rapid increase of the temperature of an end surface of the incident end 14 and finally causes destruction of the end surface of the incident end 14. From the foregoing description, it is understood that, in the laser surgical unit using the Er:YAG laser, the contact laser probe 1 must be made of a basic material containing the hydroxyl group at a concentration between 0.5 and 30 ppm.

TABLE 1

| Concentration of Hydroxyl Group (ppm) | 0.1 | 0.5 | 0.8 | 1 | 8 | 10 | 15 | 30 |
|---|---|---|---|---|---|---|---|---|
| Emitting Rate | 97 | 90 | 86 | 80 | 17 | 11 | 4 | 0 |

TABLE 1-continued

| (%) | | | | | | | | |
|---|---|---|---|---|---|---|---|---|
| Temperature of Probe (°C.) | 40 | 60 | 75 | 80 | 130 | 150 | 155 | 160 |

The operating portion 12 illustrated in FIG. 2 is made of a basic material of quartz glass with a hydroxyl group 13 contained in the basic material at a rate of 1 ppm. Containing 1 ppm of the hydroxyl group 13, the quartz glass exhibits a characteristic such that, when an incident laser beam having a wavelength of 2.94 82 m travels by 20 mm, 20% of optical energy of the incident laser beam is absorbed in the quartz glass to be converted into thermal energy. Consequently, the operating portion 12 is heated to 80° C. to form a coagulation layer in the living tissue. Thus, hemostasis is successfully carried out.

For use as a laser surgical unit, the contact laser probe 1 of the above-mentioned structure is connected to an outgoing end of an optical fiber for guiding a laser beam emitted from a laser oscillator (FIG. 1).

Figure 3:
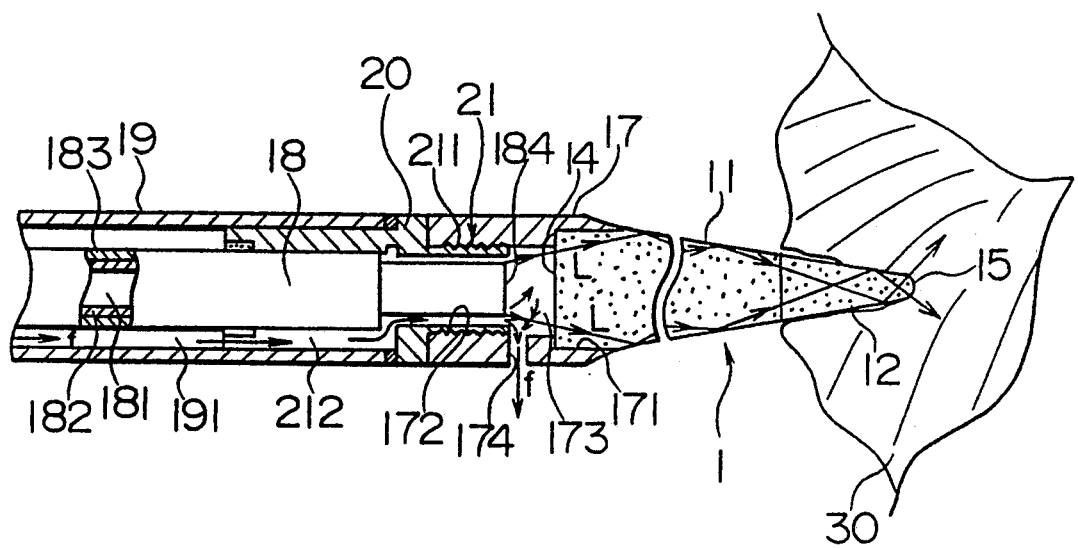
FIG. 3 is a sectional view of the contact laser probe illustrated in FIG. 2 when the contact laser probe is connected to an optical fiber.

Referring to FIG. 3, the contact laser probe 1 is connected to an outgoing end of an optical fiber 18. In the figure, a female connector 17 is fixedly attached to the base end of the contact laser probe 1. The female connector 17 has a generally cylindrical shape. The female connector 17 has an enlarged bore 171 formed adjacent to a top end thereof (a righthand side in the figure). The enlarged bore 171 is for inserting the base end of the contact laser probe 1 to be coupled thereto. The female connector 17 further has a female screw 172 formed adjacent to a base end thereof for engaging a male screw 211 of a male connector 21 which will later be described. For connection, the contact laser probe 1 is inserted in and coupled with the enlarged bore 171 of the female connector 17 while the male screw 211 of the male connector 21 is engaged with the female screw 172 of the female connector 17. In this state of connection, a space is formed between the contact laser probe 1 and the male screw 211. The space serves as a cooling chamber 173 for cooling the incident end 14 of the contact laser probe 1 and an outgoing end 184 of the optical fiber 18 which will later be described. The cooling chamber 173 communicates through a fluid discharge port 174 with the exterior so as to discharge a cooling fluid f flowing into the cooling chamber 173.

Referring again to FIG. 1, the cooling fluid f is supplied from an external cooling gas source (not shown) through a cooling gas inlet 8 formed on a socket 7 for connecting the laser beam transmitter 3 and the laser oscillator 4.

Turning back to FIG. 3, the optical fiber 18 comprises a core 181, a clad 182 surrounding the core 181, and a protection jacket 183 covering the clad 182. The optical fiber 18 is made of fluoride when an Er:YAG laser beam is used. The optical fiber 18 is received in an outer tube 19 with a top end of the optical fiber 18 fixed by a clamp member 20. The clamp member 20 is provided with the male connector 21 for coupling the optical fiber 18 and the contact laser probe 1. The male connector 21 has the male screw 211 to be engaged with the female screw 172 of the female connector 17.

A gap is formed between an outer peripheral surface of the optical fiber 18 and an inner peripheral surface of the outer tube 19. The gap serves as a fluid path 191 for guiding a cooling fluid (for example, dry air) f from the laser oscillator to the contact laser probe 1. The cooling fluid f flows through the fluid path 191 and a fluid transit slit 212 of the clamp member 20 into the cooling chamber 173 to thereby cool the outgoing end 184 of the optical fiber 18 as well as the incident end 14 of the contact laser probe 1. The cooling fluid f also serves to prevent the outgoing end 184 from being contaminated with dust. The cooling fluid f is discharged from the fluid discharge port 174 to the exterior.

With the above-mentioned structure, a laser beam L is transmitted from the laser oscillator 4 through the optical fiber 18 to be emitted out from the outgoing end 184. The laser beam L is incident through the incident end 14 of the contact laser probe 1 to reach the operating portion 12 while internal reflection is repeated within the contact laser probe 1. A part of the laser beam L reaching the operating portion 12 is absorbed in the hydroxyl group 13 contained in the basic material of the operating portion 12 to be converted into thermal energy. Consequently, the operating portion 12 is heated to 80° C. or so. A remainder of the laser beam L is uniformly emitted out from the operating portion 12.

The operating portion 12 of the contact laser probe 1 is brought into contact with a living tissue 30 to be subjected to a surgical operation. The laser beam L emitted from the operating portion 12 is absorbed in the living tissue 30 to cause vaporization and incision of the living tissue 30 to occur. Simultaneously, the operating portion 12 is heated to 80° C. or so. When the operating portion 12 thus heated is brought into contact with a cut portion of the living tissue 30, a coagulation layer is formed to perform hemostasis.

As described above, the laser surgical unit in this embodiment is operable as a contact-type instrument comprising the contact laser probe 1. Accordingly, it is readily possible with the operating portion 12 thus heated to form a coagulation layer having a sufficient thickness which is essential in hemostasis of the cut portion of the living tissue 30. In addition, an operator can feel a sense of touch. Therefore, it is possible to form a uniform coagulation layer so that hemostasis is successfully performed during incision.

The operating portion 12 comprises the basic material containing the hydroxyl group 13 at a rate of 1 ppm. A laser beam is emitted out from the operating portion 12 while the operating portion 12 is heated to 80° C. or so. The sense of touch is kept unchanged. As a result, it is possible to avoid an operation error by the operator, for example, in a cutting speed. Thus, the laser surgical unit is excellent in manipulatability and is capable of safely and uniformly perform incision and hemostasis of a living tissue.

An internal temperature of the operating portion 12 is as relatively low as 80° C. Accordingly, it is possible to avoid thermal destruction due to overheat of the operating portion 12.

Figure 4:
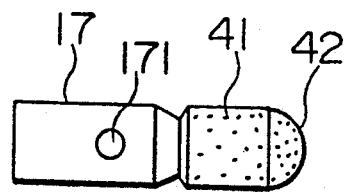
FIG. 4 is a side view of a contact laser probe according to a second embodiment of this invention.
Figure 5:
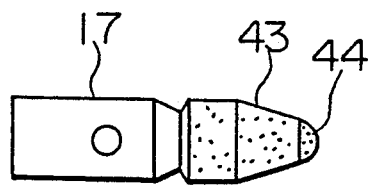
FIG. 5 is a side view of a contact laser probe according to a third embodiment of this invention.
Figure 6:
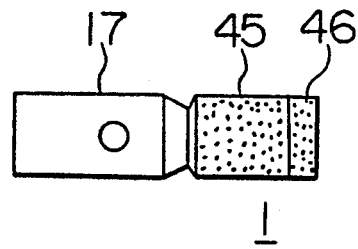
FIG. 6 is a side view of a contact laser probe according to a fourth embodiment of this invention.

In the above-mentioned embodiment, the contact laser probe 1 has a structure illustrated in FIG. 2. However, various modifications may be adopted in the structure of the contact laser probe 1. As shown in FIG. 4, the contact laser probe 1 may comprise an optical guide portion 41 of a cylindrical shape and an operating portion 42 of a spherical shape. Alternatively, an optical guide member 43 comprises a cylindrical portion adjacent to a base end and a conical portion adjacent to a top end while an operating portion 44 has a spherical shape, as shown in FIG. 5. As a further alternative shown in FIG. 6, both of an optical guide member 45 and an operating portion 46 have a cylindrical shape.

Various other shapes may be adopted in correspondence to a position of the living tissue to be operated.

Figure 7:
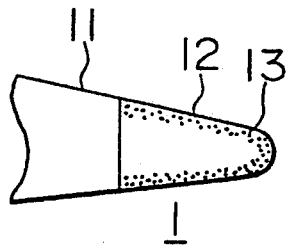
FIG. 7 is a partial side view of a contact laser probe according to a fifth embodiment of this invention.
Figure 8:
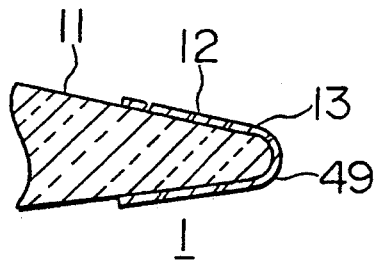
FIG. 8 is a partial side view of a contact laser probe according to a sixth embodiment of this invention.

The operating portion 12 may include the hydroxyl group 13 throughout an entire internal area of the operating portion 12. Alternatively, the hydroxyl group 13 may be dispersed in the operating portion 12 only in an area adjacent to a surface of the operating portion 12, as shown in FIG. 7. In order to make the hydroxyl group 13 be contained in the area adjacent to the surface of the operating portion 12, the hydroxyl group 13 may be dispersed in the basic material of the operating portion 12. Alternatively, as shown in FIG. 8, a thin film 49 including the hydroxyl group 13 may be attached to the surface of the operating portion 12 by the use of vapor deposition, sputtering, ion plating, CVD, a sol-gel method, or the like. In this modification, thermal destruction is avoided even if the basic material has a relatively low heat-resistance. In addition, the surface of the operating portion 12 is exclusively heated to form a coagulation layer while the laser beam is allowed to be emitted out from the operating portion 12 with high efficiency.

Figure 9:
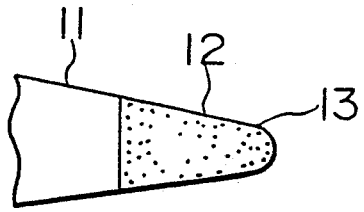
FIG. 9 is a partial side view of a contact laser probe according to a seventh embodiment of this invention.

Referring to FIG. 9, the contact laser probe 1 is formed by combining the optical guide portion 11 for transmitting the laser beam and the operating portion 12 made of the basic material containing the hydroxyl group 13, for example, by the use of a fusion-bonding technique. In this embodiment also, the operating portion 12 is exclusively heated while the laser beam is allowed to be emitted out from the operating portion 12 with high efficiency.

Figure 10:
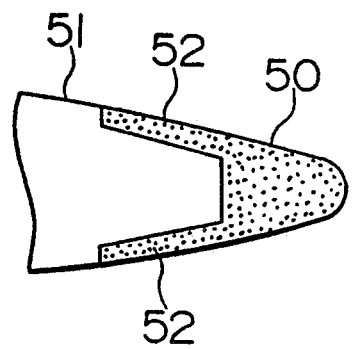
FIG. 10 is a partial side view of a contact laser probe according to an eighth embodiment of this invention.

FIG. 10 is a further modification of the contact laser probe 1 illustrated in FIG. 9. As shown in FIG. 10, an operating portion 50 is provided at a base end thereof with a skirt portion 52 extending towards an optical guide portion 51 so as to heat a wider area.

Figure 11:
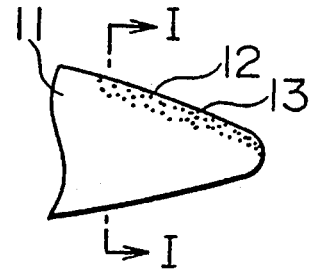
FIG. 11 is a partial side view of a contact laser probe according to a ninth embodiment of this invention.
Figure 12:
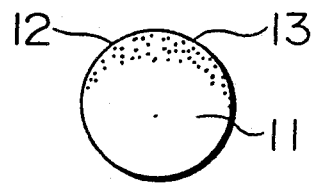
FIG. 12 is a sectional view taken along line I—I in FIG. 11.

FIGS. 11 and 12 show a further modification of the contact laser probe 1 illustrated in FIG. 7. FIG. 11 is a sectional view of a tip of the contact laser probe 1 according to this modified embodiment. FIG. 12 is a sectional view taken along a line I—I in FIG. 11. As shown in the figure, the hydroxyl group 13 is partially included in the operating portion 12 only in a portion adjacent to one side surface of the tip of the contact laser probe 1. Thus, the one side surface of the tip of the contact laser probe 1 is exclusively heated to form a coagulation layer in a particular portion of the living tissue 30.

In the above-mentioned embodiment, the operating portion 12 comprises the basic material and the hydroxyl group 13 contained in the basic material at a rate of 1 ppm. When the content of the hydroxyl group 13 is increased, the operating portion 12 is heated to a higher temperature to increase a thickness of a coagulation layer. The content of the hydroxyl group 13 is selected in dependence upon a type of application. Specifically, an appropriate temperature for hemostasis is different in dependency upon a position of the living tissue 30 and will be selected within a range between 50° C. and 200° C., preferably, between 50° C. and 100° C. in dependency upon the position to be operated.

In the above-mentioned embodiment, use is made of the laser beam having an oscillation wavelength of 2.94 $\mu$m. It is noted here that a similar effect is obtained with the laser beam within a wavelength range between 1.5 and 15 82 m as described in the foregoing embodiment.

As thus far been described, according to this invention, the laser surgical unit is used as a contact-type instrument comprising the contact laser probe. The tip of the contact laser probe is heated to form the coagulation layer for hemostasis in the cut portion of the living tissue. In addition, the operator can feel a sense of touch in a surgical operation. Accordingly, the laser surgical unit is excellent in manipulatability, capable of uniformly forming the coagulation layer, and capable of successfully carrying out hemostasis during incision.

What is claimed is:

1. A laser surgical unit for use in a surgical operation to perform vaporization and incision of a living tissue, said laser surgical unit comprising:
   a laser generator for generating a laser beam of a predetermined wavelength;
   an optical guide which has a first end optically coupled to said laser generator and a second end opposite said first end for guiding said laser beam from said first end to said second end; and
   a contact laser probe which is connected to said second end of the optical guide to emit said laser beam on living tissue and which includes a specific portion comprising a hydroxyl group in an amount between 0.5 and 10 ppm.

2. A laser surgical unit as claimed in claim 1, said contact laser probe having a support portion and a tip portion supported by said support portion to emit said laser beam through said tip portion, wherein said specific portion is restricted to said tip portion.

3. A laser surgical unit as claimed in claim 2, wherein said tip portion is coated with a coating film containing the hydroxyl group.

4. A laser surgical unit as claimed in claim 1, wherein said specific portion is restricted to a surfacial area of said contact laser probe.

5. A laser surgical unit as claimed in claim 1, wherein said laser beam has a wavelength between 1.5 through 15 $\mu$m.

6. A laser surgical unit as claimed in claim 1, wherein said laser beam is selected from the group consisting of an Er:YAG laser beam, a Ho:YAG laser beam, and a $CO_2$ laser beam.

7. A laser therapeutic method comprising the steps of providing a contact laser probe including a hydroxyl group in an amount of between 0.5 and 10 ppm, bringing the contact laser probe into contact with living tissue, delivering a laser beam from said contact laser probe, and irradiating said living tissue by said laser beam to perform vaporization and incision of said living tissue while said contact laser probe is heated by a portion of said laser beam absorbed in said contact laser probe, to perform hemostasis in said living tissue.

* * * * *